(12) United States Patent
Vezzani

(10) Patent No.: US 8,114,990 B2
(45) Date of Patent: Feb. 14, 2012

(54) PROCESS FOR DRYING MELAMINE

(75) Inventor: Corrado Vezzani, Rozzano (IT)

(73) Assignee: Vomm Impianti E Processi S.p.A., Rozzano (IT)

( * ) Notice: Subject to any disclaimer, the term of this patent is extended or adjusted under 35 U.S.C. 154(b) by 799 days.

(21) Appl. No.: 12/162,437

(22) PCT Filed: Jan. 25, 2007

(86) PCT No.: PCT/EP2007/000636
§ 371 (c)(1),
(2), (4) Date: Oct. 7, 2008

(87) PCT Pub. No.: WO2007/085450
PCT Pub. Date: Aug. 2, 2007

(65) Prior Publication Data
US 2009/0176982 A1    Jul. 9, 2009

(30) Foreign Application Priority Data

Jan. 30, 2006  (EP) .................................... 06425039

(51) Int. Cl.
*C07D 251/62* (2006.01)
*C07D 251/60* (2006.01)
(52) U.S. Cl. ....................................... 544/203; 544/201

(58) Field of Classification Search .................. 544/201, 544/203
See application file for complete search history.

(56) References Cited

U.S. PATENT DOCUMENTS 5,409,643 A * 4/1995 Vezzani ............................. 264/8

FOREIGN PATENT DOCUMENTS

| EP | 0 530 903 A1 | 3/1993 |
| WO | WO 99/54316 | 10/1999 |

* cited by examiner

*Primary Examiner* — Venkataraman Balasubramanian
(74) *Attorney, Agent, or Firm* — Lucas & Mercanti, LLP

(57) ABSTRACT

A process is described for drying melamine wet cakes, comprising the steps of: a) providing a turbo-dryer (T) comprising a cylindrical tubular body (1) having a heating jacket (4), inlets and outlets (5, 6) and a bladed rotor (7) rotatably supported therein; b) feeding a continuous flow of a melamine wet cake into the turbo-dryer (T), the internal wall (9) of which is maintained at a temperature of at least 220° C.; c) feeding a continuous flow of a gas selected from air or nitrogen into the turbo-dryer (T); d) subjecting the flow of melamine wet cake to the mechanical action of the bladed rotor (7) rotating at a speed of at least 200 rpm, with consequent centrifugation of the wet cake against the heated wall (9), thus causing the instantaneous evaporation of the water contained into the cake, and transport of the latter towards the outlet (6); e) continuously discharging, after an average residence time of less than 1 minute, a flow of melamine crystals having a humidity content of less than 0.1%.

8 Claims, 1 Drawing Sheet

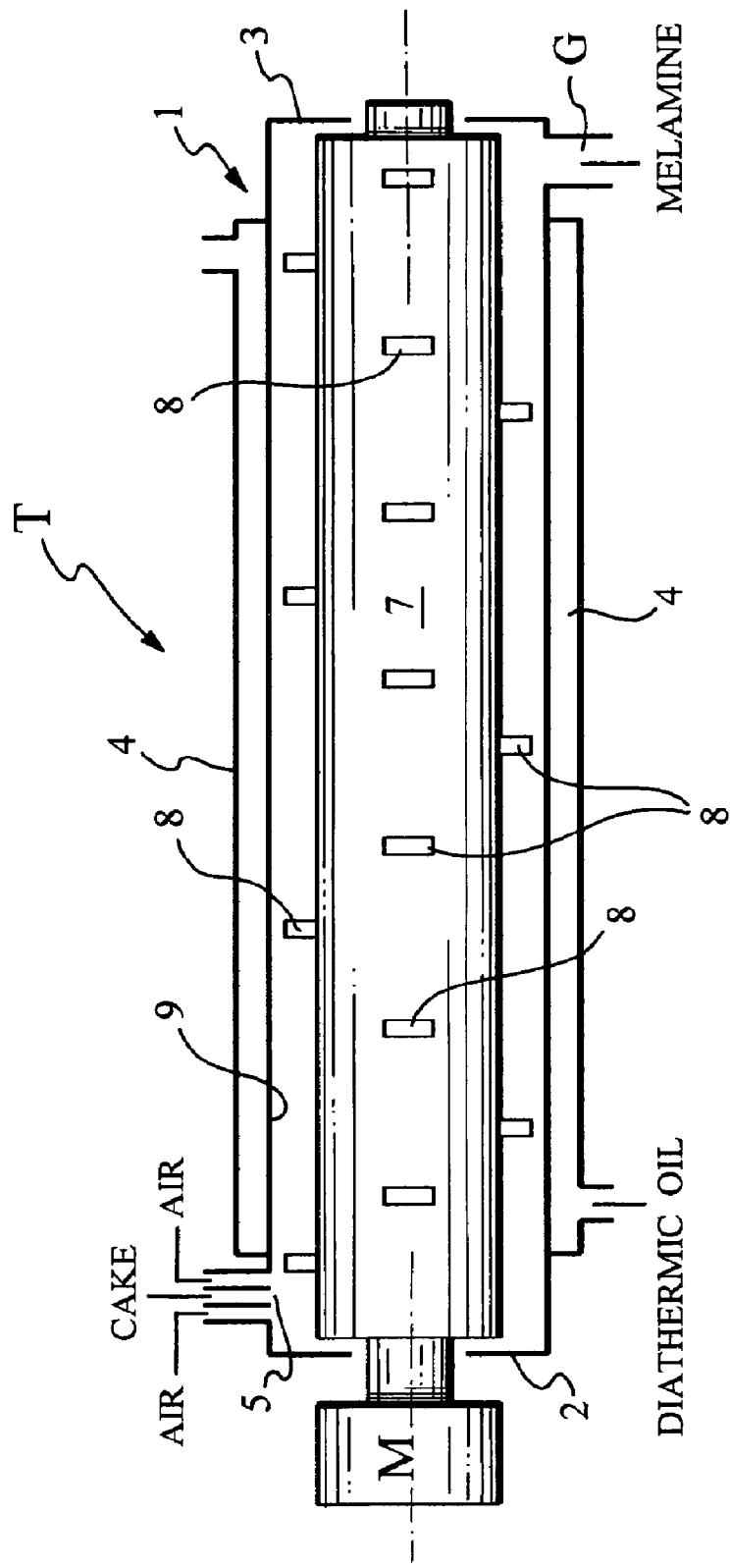
Figure

PROCESS FOR DRYING MELAMINE

FIELD OF APPLICATION

The present invention relates in general to the technical field of the chemical industry. In particular, the invention relates to a process for drying melamine wet cakes.

PRIOR ART

A number of processes for the production of melamine have long been known (please see, for example, U.S. Pat. No. 3,598,818, EP 0 091 174 and WO 95/06042), which involve the formation, at a certain stage, of a slurry of water and melamine crystals, wherein a variable quantity of ammonia is dissolved.

A number of purification methods, comprising re-crystallisation steps, are available for obtaining melamine of suitable purity, which ultimately lead to the formation of a melamine crystals wet cake having a predetermined particle size.

The drying of the above-mentioned cake may be carried out in various ways and typically by a flash dryer. As explained in application EP 1 071 673, however, the use of a flash dryer involves some inconveniences, first of all the production of a considerable amount of so-called "fine" particles; that is, having a diameter of less than 21 µm, which as a consequence causes a decrease in the apparent density and in the compacted density, which affects the ease of transport and processing of the end product.

In order to improve the apparent density and the compacted density of the dried melamine, application EP 1 071 673 suggests the use of a different method for drying the melamine wet cake. Such method involves the use of a contact dryer, that is, a dryer wherein heat is applied to the wet cake mainly by contact with the surfaces of the dryer (for example a tube bundle, a revolving drum or a cabinet dryer).

The drying of the melamine cake is carried out by keeping the dryer wall in contact with the cake to be dried at a temperature between 100 and 220° C. and preferably between 120 and 160° C., with a residence time comprised between 0.1 and 10 hours (preferably 1-3 hours).

By operating in this way, an end product is obtained, having a humidity content of less than 0.1% on a wet basis and a content of fine particles having a diameter smaller than 21 µm of less than 30% by weight. In any case, using the method according to EP 1 071 673, a percentage of fine particles is obtained which is lower than that which would be obtained using the conventional technique that uses the flash dryer.

However, it will be appreciated that the time required to carry out the drying of the melamine wet cake by contact is considerably longer than that required when using a flash dryer, with a consequent slow-down in the production cycles.

SUMMARY OF THE INVENTION

The problem at the basis of the present invention was that of providing a process for drying melamine wet cakes which would allow to obtain an end product having good apparent density and compacted density properties as well as to meet all the requirements of the regulations in force in considerably shorter times than those involved in the method according to EP 1 071 673.

Such a problem has been solved by a process which comprises the steps of:

providing a turbo-dryer comprising a cylindrical tubular body having a heating jacket, inlets and outlets and a bladed rotor rotatably supported therein, feeding a continuous flow of a melamine wet cake into the turbo-dryer, the internal wall temperature of which is at least 120°, feeding a continuous flow of a gas selected from air or nitrogen into the turbo-dryer, subjecting the flow of melamine wet cake to the mechanical action of the bladed rotor rotating at a speed of at least 200 rpm, with consequent centrifugation of the above wet cake against the heated wall, thus causing the instantaneous evaporation of the water contained in the cake, and transport of the latter towards the outlet, continuously discharging, after an average residence time of less than 300 seconds, a flow of melamine crystals with a humidity content of less than 0.1%.

Preferably, the temperature of the internal wall of the turbo-dryer is comprised between 225° C. and 280° C. and the gas introduced into the turbo-dryer is air heated to 120-200° C., which can be introduced both co-currently and counter-currently relative to the wet cake flow.

The air flow rate is generally comprised between 200 and 800 $Nm^3/h$ for every 100 kg of wet product fed.

The rotation speed of the bladed rotor is preferably comprised between 200 and 1500 rpm.

The residence time of the melamine cake inside the turbo-dryer is generally comprised between 15 and 100 seconds.

The process according to the present invention shall be further described with reference to a drawing and to an embodiment provided only for illustrative and non-limiting purposes.

BRIEF DESCRIPTION OF THE DRAWINGS

In the one drawing annexed, a drying equipment used for carrying out the process according to the present invention is shown.

DETAILED DESCRIPTION OF A PREFERRED EMBODIMENT

With reference to such drawing, the equipment used for drying melamine wet cakes comprises a turbo-dryer T.

Turbo-dryer T (manufactured, for example, by the company VOMM Impianti e Processi, Rozzano (MI)) essentially comprises a cylindrical tubular body 1 closed at the opposite ends by bottom walls 2, 3 and having a coaxial heating jacket 4 to be run through by a fluid, for example diathermic oil.

The tubular body 1 has an inlet 5 for the melamine wet cake and for the gas flow and an outlet 6 for the product that has undergone the drying treatment.

A bladed rotor 7 is rotatably supported inside the tubular body 1. The rows of blades 8 of this rotor are helically arranged and oriented so as to centrifuge and simultaneously convey the product subjected to drying towards the outlet. A motor M makes rotor 7 rotate at a speed comprised between 200 and 1500 rpm, preferably 400-600 rpm.

Obviously, for technical reasons of a contingent nature, the turbo-dryer may exhibit more than one inlet and/or outlet.

A flow of a melamine wet cake is continuously fed into the turbo-dryer T through the inlet 5, simultaneously and co-currently relative to a flow of heated air. The melamine wet cake is centrifuged by the rotor blades, upon its entrance into the turbo-dryer, against the internal heated wall 9 and at the same time it is conveyed towards the outlet 6 thanks to the helical orientation of the above-mentioned blades.

Thanks to the formation of a thin, dynamic, turbulent tubular layer of melamine cake, wherein the single particles absorb a very large amount of energy, both in the form of mechanical energy given by the action of the bladed rotor rotating at a high speed, and in the form of heat released from the internal heated wall of the turbo-dryer T and from the hot air, the water contained in the melamine wet cake undergoes instantaneous evaporation.

After a residence time of about 15-60 seconds inside the turbo-dryer, a flow of melamine crystals with a humidity content of less than 0.1% is continuously discharged.

It should be noted that the hot air flow may also be fed counter-currently relative to the flow of melamine wet cake, through the outlet 6 or through a further outlet formed in the proximity of bottom wall 3. Irrespective of the feeding direction thereof, the hot air flow considerably facilitates the removal of the vapour generated by the evaporation of the water contained in the cake and allows the complete removal of the ammonia that is frequently found dissolved in such water.

EXAMPLE

Using the equipment schematically described above and following the method of the invention, a melamine wet cake having a content of fine particles (diameter of less than 21 μm) of 2.5% and a water content of 12% (measured at 105° C.), wherein ammonia in a percentage of 14% (by weight of such water) was dissolved, was continuously fed into the turbo-dryer T, at a rate of 80 Kg/h, simultaneously and co-currently relative to an air flow at 200° C., having a rate of 300 Nm$^3$/h.

The temperature of wall 9 was maintained at about 250° C. while the rotation speed of the bladed rotor 7 was kept constant at 700 rpm.

After an average residence time of about 60 seconds inside the turbo-dryer T, a flow of air mixed with steam and a flow of melamine crystals, having an apparent density of 0.74, free of ammonia and having a humidity content of 0.04%, were continuously discharged. The content of fine particles (diameter of less than 21 μm) of the dried product was of 3.4%, its titre was 99.9% and its grade of whiteness, measured according to APHA (that is, by visual comparison with a scale of specimens made of potassium chloroplatinat diluted in formaldehyde) was 10.

The invention claimed is:

1. A process for drying a melamine wet cake, comprising the steps of:
    providing a turbo-dryer comprising a cylindrical tubular body having a heating jacket, inlets and outlets and a bladed rotor rotatably supported therein,
    feeding a continuous flow of said melamine wet cake into said turbo-dryer, the internal wall of which is maintained at a temperature of at least 220° C.,
    feeding a continuous flow of a gas selected from air or nitrogen into said turbo dryer,
    subjecting said flow of said melamine wet cake to the mechanical action of said bladed rotor rotating at a speed of at least 200 rpm, with consequent centrifugation of said wet cake against said heated wall, thus causing the instantaneous evaporation of the water contained in the cake, and transport of the latter towards the outlet,
    continuously discharging, after an average residence time of less than 300 seconds, a flow of melamine crystals having a humidity content of less than 0.1%.

2. Process according to claim 1, wherein the temperature of the internal wall of said turbo-dryer is comprised between 225° C. and 280° C.

3. Process according to claim 2, wherein the gas introduced into the turbo-dryer is air heated to 120-240° C.

4. Process according to claim 3, wherein said heated air flow is fed co-currently relative to said melamine wet cake flow.

5. Process according to claim 3, wherein said heated air flow is fed counter-currently relative to said melamine wet cake flow.

6. Process according to claim 3, wherein the rate of said air flow is comprised between 200 and 800 Nm$^3$/h for every 100 kg of fed melamine wet cake.

7. Process according to claim 1, wherein the rotation of said bladder rotor is comprised between 200 and 1500 rpm.

8. Process according to claim 1, wherein the residence time of the melamine cake inside said turbo-dryer is comprised between 15 and 100 seconds.

* * * * *